United States Patent
Kario et al.

(10) Patent No.: US 7,018,335 B2
(45) Date of Patent: Mar. 28, 2006

(54) BLOOD PRESSURE MONITOR AND CARDIOVASCULAR DISEASE RISK ANALYZING PROGRAM

(75) Inventors: Kazuomi Kario, Minamikawachi-cho (JP); Osamu Shirasaki, Osaka (JP)

(73) Assignee: Omron Healthcare Co., Ltd., Kyoto (JP)

( * ) Notice: Subject to any disclaimer, the term of this patent is extended or adjusted under 35 U.S.C. 154(b) by 39 days.

(21) Appl. No.: 10/697,651

(22) Filed: Oct. 31, 2003

(65) Prior Publication Data
US 2004/0176692 A1 Sep. 9, 2004

(30) Foreign Application Priority Data
Mar. 3, 2003 (JP) .............................. 2003-056052

(51) Int. Cl.
*A61B 5/02* (2006.01)
(52) U.S. Cl. ........................................ 600/485; 600/481
(58) Field of Classification Search ........ 600/300–301, 600/485–507
See application file for complete search history.

(56) References Cited

U.S. PATENT DOCUMENTS

| | | | | | |
|---|---|---|---|---|---|
| 5,398,696 | A | * | 3/1995 | Wiley | ........................ 600/587 |
| 6,355,000 | B1 | * | 3/2002 | Ogura | ........................ 600/490 |
| 6,699,195 | B1 | * | 3/2004 | Nakazawa et al. | .......... 600/485 |
| 6,808,497 | B1 | * | 10/2004 | Ogura et al. | ................ 600/490 |

* cited by examiner

*Primary Examiner*—Robert L. Nasser
*Assistant Examiner*—Patricia Mallari
(74) *Attorney, Agent, or Firm*—Morrison & Foerster LLP

(57) ABSTRACT

A blood pressure monitor associates information representing measuring time input from a clock with measured blood pressure values so as to store them in a memory. Blood pressure values measured in a morning time zone and blood pressure values measured in an evening time zone are grouped based on the time information associated with the blood pressure values so as to be stored in the memory. A data intra-group average calculating section calculates averages of the blood pressure values in the groups, and a risk calculating section calculates a risk value based on the calculated results of the data intra-group average calculating section.

28 Claims, 10 Drawing Sheets

US 7,018,335 B2

BLOOD PRESSURE MONITOR AND CARDIOVASCULAR DISEASE RISK ANALYZING PROGRAM

CLAIM FOR PRIORITY

This application claims the benefit to Japanese application No. 056052/2003, which was filed on Mar. 2, 2003, the contents of which are hereby incorporated by reference.

TECHNICAL FIELD OF THE INVENTION

The present invention relates to a blood pressure monitor and a risk analyzing program. Particularly, the invention relates to the blood pressure monitor and a cardiovascular disease risk analyzing program which can provide information about cardiovascular risk.

BACKGROUND OF THE INVENTION

According to recent spread of self-medication, equipment for measuring blood pressure at home is quickly being diffused in general home.

Blood pressure monitors for home use, which are being diffused now, have a function for displaying blood pressure levels with large diffusion at different times as measured values, or a function for sounding a buzzer to inform patients of a degree of risk when a value at one-time measurement exceeds a certain value. Further, for example, a patent document 1 (Japanese Patent Application Laid-Open No. 11-33003 (1999)) discloses a blood pressure monitor for measuring blood pressure from normal time via a constant moving load to return to normal state and analyzing ventricular function of patients.

The blood pressure is a barometer of analysis, and it is effective for preventing of cardiovascular diseases such as cerebral apoplexy, cardiac failure and myocardial infarct to analyze the risk based on the blood pressure.

For example, in a document other than the Patent Document 1 (Kario Nanaomi, "Risk of early-morning high blood pressure and cerebrovascular disease" "Journal of Blood Pressure" November", Sentan Igaku-sha, Nov. 1, 2002, vol. 9, no. 11, p. 94–97), the inventors of this application refer to relation between abrupt rise in blood pressure and the cerebral apoplexy which is their studied result. Such abrupt rise in the blood pressure is called as morning surge and occurs one to one and half hour after uprising. Further, the inventors describe necessity of obtaining interrelation of a change in blood pressure when the risk of cardiovascular diseases is analyzed.

The blood pressure has intra-day fluctuating rhythm such that the blood pressure changes due to individual physical activity, reaction to a stress, reaction of cardiovascular system to behavior pattern and the like, the blood pressure drops at night time but rises before and after awakening in the morning. Prior blood pressure monitors, however, display a fluctuation of the blood pressure simply along a time base or represent a grade of the fluctuation only with numerical values statistically.

The prior blood pressure monitors disclosed in Patent Document 1, however, have a problem such that it is not provided with a following function. The function is for synthetically analyzing and evaluating information about a blood pressure measured value which changes with age according to a blood pressure value and aged deterioration of variability. Further, the function is for estimating individual cardiovascular risk so as to inform patients or doctors of the estimated cardiovascular risk as information which is used for blood pressure management cure.

SUMMARY OF THE INVENTION

The present invention provides a blood pressure monitor and a cardiovascular disease risk analyzing program which provide information about cardiovascular risk analyzed and evaluated based on a blood pressure level measured at patients' home, variability and aged deterioration so as to facilitate selection of blood pressure self-evaluation and management by patients and antihypertensive therapy by doctors and enable optimal antihypertensive management and curing at an early date.

According to one embodiment of the present invention, a blood pressure monitor includes a blood pressure data storage unit for storing blood pressure data groups each of which includes at least one blood pressure datum measured under one measuring condition per measuring condition; and an evaluating quantity calculating unit for calculating an evaluating quantity based on interrelation between the blood pressure data in the blood pressure data groups and the blood pressure data in another blood pressure data groups with different measuring condition.

In one aspect, the blood pressure monitor further includes an intra-group average calculating unit for calculating intra-group averages of blood pressure data in the blood pressure data groups for the blood pressure data groups with the different measuring conditions.

In another aspect, the evaluating quantity calculating unit calculates the evaluating quantity based on an average value and a different value of the intra-group averages in the blood pressure data groups.

In another aspect, the evaluating quantity is related with a degree of a risk of cardiovascular diseases.

In still another aspect, the measuring conditions are a plurality of specified time zones.

In addition, it is preferable that the plural specified time zones include a first time zone which starts from about two hours before bedtime and ends until two hours after bedtime, and a second time zone which starts from about two hours before uprising and ends until about two hours after uprising.

In yet another aspect, the blood pressure monitor further includes a clock unit for outputting time information. The blood pressure data storage unit discriminates the measuring conditions for each blood pressure data based on the time information output from the clock unit and stores the blood pressure data according to measuring conditions.

In another aspect, the blood pressure monitor further includes an input unit through which a user inputs the measuring conditions. The blood pressure data storage unit stores the blood pressure data based on the measuring conditions input from the input unit.

Further, it is preferable that the blood pressure monitor further includes a diagnostic unit for providing at least one or more threshold values on at least one of primary parameter axes obtained as intra-group averages of a plurality of blood pressure data groups with the different measuring conditions or average values and different values of the intra-group averages, defining a plurality of primary parameter areas, which are prescribed by the threshold values, in a primary parameter multi-dimensional area composed of the primary parameter axes, and determining or displaying which area of the primary parameter areas where actual values of primary parameters obtained based on the measured blood pressure data are present, so as to make a diagnosis based on the blood pressure data.

Further, it is preferable that the blood pressure monitor further includes a primary parameter area display unit for displaying the primary parameter multi-dimensional area. The primary parameter area display unit displays the actual values of the primary parameters on the primary parameter multi-dimensional area.

In still another aspect, the blood pressure monitor further includes a primary parameter set storage unit for storing a plurality of primary parameter sets which are composed of the intra-group averages of the blood pressure data groups with the different measuring conditions or pairs of the average values and the different values of the intra-group averages. The primary parameter area display unit displays the primary parameter sets on the primary parameter multi-dimensional area simultaneously.

In yet another aspect, the blood pressure monitor further includes a cardiovascular disease risk defining unit in which a degree of digitized cardiovascular disease risk is associated with the primary parameter areas, respectively. The risk calculating unit determines or displays the cardiovascular disease risk based on the determination as to which area of the primary parameter areas where the actual values of the primary parameters are present.

In one aspect, the threshold values provided on the primary parameter axes obtained as the average values of the intra-group averages in the blood pressure data groups are threshold values of systolic blood pressure, and they are about 135 mmHg.

In another aspect, the different values of the intra-group averages in the blood pressure data groups are increments of systolic blood pressure measured at time before and after uprising with respect to systolic blood pressure measured at time before bedtime, and the threshold values provided on the primary parameter axes obtained as the different values of the intra-group averages are about 20 mmHg.

In yet another aspect, the blood pressure monitor further includes a cardiovascular disease risk calculating function unit for estimating a degree of cardiovascular disease risk in a numerical manner by using both the average values and the different values of the intra-group averages in the blood pressure data groups as input variables. The cardiovascular disease risk calculating function unit calculates or displays the cardiovascular disease risk when the actual values of the average values and the different values of the intra-group averages are obtained.

In another embodiment of the invention, a cardiovascular disease risk analyzing program allows a computer to execute the obtaining step of obtaining blood pressure data; the blood pressure data storing step of storing blood pressure data groups including at least one blood pressure datum measured under same measuring conditions in the obtained blood pressure data into a storage section according to measuring conditions; and the evaluating quantity calculating step of calculating an evaluating quantity based on interrelation between the blood pressure data in the blood pressure data group and the blood pressure data in another blood pressure data group with different measuring condition.

Further, it is preferable that the cardiovascular disease risk analyzing program allows the computer to further execute the intra-group average calculating step of calculating intra-group averages of the blood pressure data in the blood pressure data groups for the blood pressure data groups with the different measuring conditions.

In one aspect, the evaluating quantity calculating step, the evaluating quantity is calculated based on average values and different values of the intra-group averages in the blood pressure data groups.

In another aspect, the evaluating quantity relates to a degree of the cardiovascular disease risk.

In still another aspect, the measuring conditions are a plurality of specified time zones.

In yet another aspect, the specified time zones include a first time zone which starts from about two hours before bedtime and ends until about two hours after bedtime, and a second time zone which starts from about two hours before uprising and ends until about two hours after uprising.

In still another aspect, the cardiovascular disease risk analyzing program allows the computer to further execute the clock step of outputting time information. At the blood pressure data storing step, the measuring conditions are discriminated according to the blood pressure data based on the time information output at the clock step, and the blood pressure data are stored into the storage section according to the measuring conditions.

In another aspect, the cardiovascular disease risk analyzing program allows the computer to further execute the input step of receiving the measuring conditions from a user. At the blood pressure data storing step, the blood pressure data are stored based on the measuring conditions input at the input step into the storage section according to the measuring conditions.

It is preferable that the cardiovascular disease risk analyzing program allows the computer to further execute the diagnostic step of providing one or more threshold values on at least one of primary parameter axes obtained as the intra-group averages in the blood pressure data groups with the different measuring conditions or the average values and the different values of the intra-group averages, defining a plurality of primary parameter areas which are prescribed by the threshold values in a primary parameter multi-dimensional area composed of the primary parameter axes, and determining or displaying as to which area of the primary parameter areas where actual values of primary parameters obtained based on the measured blood pressure data are present so as to make a diagnosis based on the blood pressure data.

In another aspect, the cardiovascular disease risk analyzing program allows the computer to further execute the primary parameter area display step of displaying the primary parameter multi-dimensional area. At the primary parameter area display step, the actual values of the primary parameters are displayed on the primary parameter multi-dimensional area.

In yet another aspect, the cardiovascular disease risk analyzing program allows the computer to further execute the primary parameter set storing step of storing a plurality of primary parameter sets composed of the intra-group averages in the blood pressure data groups with the different measuring conditions or pairs of the average values and the different values of the intra-group averages. At the primary parameter area display step, the primary parameter sets are displayed on the primary parameter multi-dimensional area simultaneously.

In another aspect, the cardiovascular disease risk analyzing program allows the computer to further execute the cardiovascular disease risk defining step of associating a degree of the digitized cardiovascular disease risk with the primary parameter areas, respectively. At the risk calculating step, the cardiovascular disease risk is determined or displayed based on the determination as to which area of the primary parameter areas where the actual values of the primary parameters are present.

In another aspect, the threshold values provided on the primary parameter axes obtained as the average values of the intra-group averages in the blood pressure data groups are threshold values of systolic blood pressure and are about 135 mmHg.

In one aspect, the different values of the intra-group averages in the blood pressure data groups are increments of systolic blood pressure measured at time before and after uprising with respect to systolic blood pressure measured at time before bedtime, and the threshold values provided on the primary parameter axes obtained as the different values of the intra-group averages are about 20 mmHg.

In another aspect, the cardiovascular disease risk analyzing program allows the computer to further execute the cardiovascular disease risk calculating function step of estimating a degree of the cardiovascular disease risk in a numerical manner by using both the average values and the different values of the intra-group averages in the blood pressure data groups as input variables. At the cardiovascular disease risk calculating function step, when the actual values of the average values and the different values of the intra-group averages are obtained, the cardiovascular disease risk is calculated or displayed.

DESCRIPTION OF THE PREFERRED EMBODIMENTS

Figure 1:
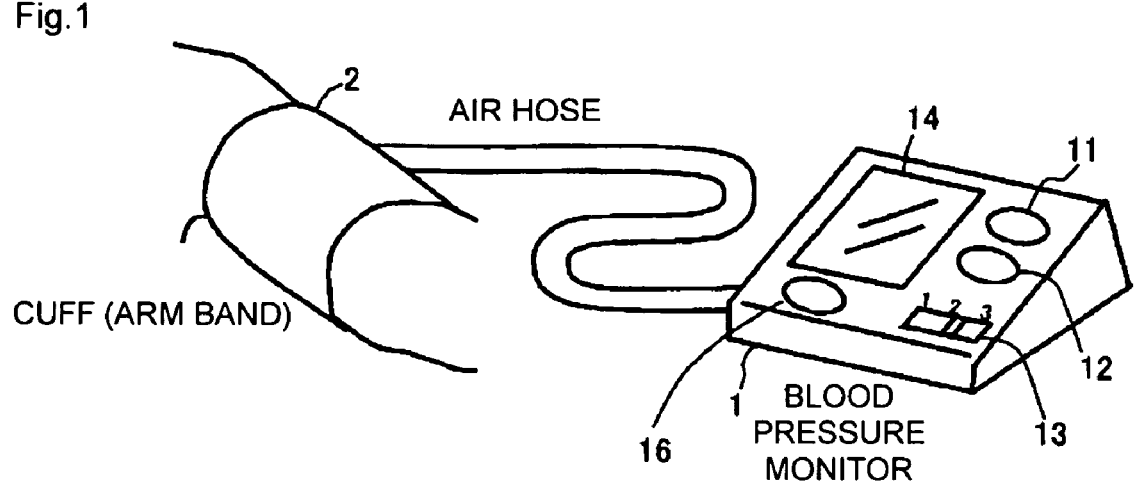
FIG. 1 is a diagram illustrating a concrete example of appearance of a blood pressure monitor 1 according to an embodiment of the present invention.

The embodiments of the present invention are explained below with reference to the drawings. In the following description, like parts and components are designated by like reference numerals. Names and functions of like parts and components are the same. Detailed explanation thereof, therefore, is not repeated.

FIG. 1 illustrates a concrete example of appearance of a blood pressure monitor 1 according to an embodiment. With reference to FIG. 1, a main body of the blood pressure monitor 1 is connected with a cuff (arm band) 2 by an air hose. Patients or doctors attach the cuff 2 to patient's extremity such as upper arm or a wrist and measure blood pressure. The measurement of blood pressure is controlled by a microprocessor 15 (see FIG. 2) included in the blood pressure monitor 1.

With reference to FIG. 1, the surface of the blood pressure monitor main body is provided with a power supply switch 11, a starting switch 12, a condition switch 13, a period setting switch 16 and a display section 14. The power supply switch 11 performs ON/OFF operation of the power supply of the blood pressure monitor 1. The starting switch 12 instructs starting of the measurement of blood pressure. The condition switch 13 inputs condition at the time of the measurement of blood pressure. The period setting switch 16 sets a period for checking transition of a blood pressure value, mentioned later. The display section 14 is composed of a liquid crystal panel or the like and displays a measured result or the like.

Figure 2:
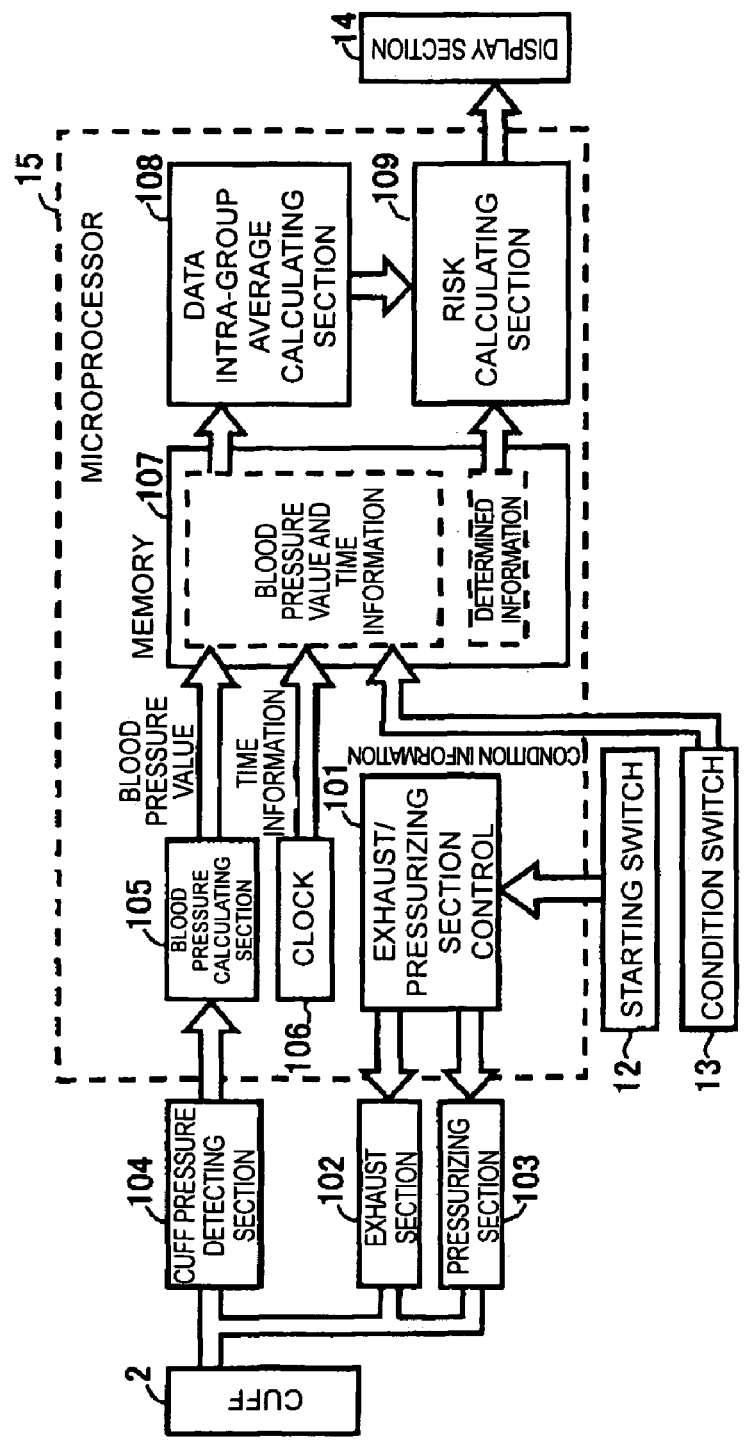
FIG. 2 is a block diagram illustrating a concrete example of a constitution of the blood pressure monitor 1.

FIG. 2 is a block diagram illustrating a concrete example of a constitution of the blood pressure monitor 1. The constitution of the blood pressure monitor 1 shown in FIG. 2 is the concrete example of the constitution when blood pressure is measured by the blood pressure monitor 1 which adopts an oscillometric type blood pressure measuring principle. The blood pressure measuring principle is one concrete example, and the present invention is not limited to this principle.

With reference to FIG. 2, the blood pressure monitor 1 includes an exhaust section 102, a pressurizing section 103 and a cuff pressure detecting section 104 which perform operations for measuring blood pressure at the cuff 2, and a microprocessor 15 which controls calculation of a blood pressure value and risk analysis in the blood pressure monitor 1.

An exhaust/pressurizing section control section 101 in the microprocessor 15 receives a control signal for instructing starting of the measurement of the blood pressure from the starting switch 12. The exhaust/pressurizing section control section 101 transmits a control signal so as to operate the exhaust section 102 for exhausting air injected into the cuff 2 and the pressurizing section 103 for injecting air into the cuff 2 so as to pressurize it.

That is to say, when the starting switch 12 is pressed down in order to measure patient's blood pressure using the blood pressure monitor 1, the control signal is input into the exhaust/pressurizing section control section 101. The exhaust/pressurizing section control section 101 operates the pressurizing section 103.

When the control signal is input from the exhaust/pressurizing section control sections 101, the pressurizing section 103 injects air into the cuff 2 until internal pressure of the cuff 2 (hereinafter, cuff pressure) becomes predetermined pressure. In such a manner the cuff pressure is applied to the cuff 2. Further, the control signal is input into the exhaust section 102 from the exhaust/pressurizing section control section 101, the exhaust section 12 exhausts the air injected into the cuff 2 so as to depressurize the cuff 2.

The cuff pressure detecting section 104 includes a pressure sensor, and captures pulse beats from patient's artery superposed on a cuff pressure signal as well as the cuff pressure which pressurizes the artery. The detected result in the cuff pressure detecting section 104 is input into a blood pressure calculating section 105 included in the microprocessor 15.

The blood pressure calculating section 105 in the microprocessor 15 calculates a blood pressure value of a patient's diseased part based on the detected result input from the cuff pressure detecting section 104. The concrete blood pressure value includes systolic blood pressure, diastolic pressure and the like. The blood pressure calculating section 105 inputs the calculated blood pressure value into a memory 107 in the microprocessor 15. The condition switch 13 inputs condition information about the measurement instructed by a user into the memory 107.

The memory 107 stores the blood pressure value input from the blood pressure calculating section 105 and the condition information input from the condition switch 13 which are associated with each other into a predetermined area.

Figure 3:
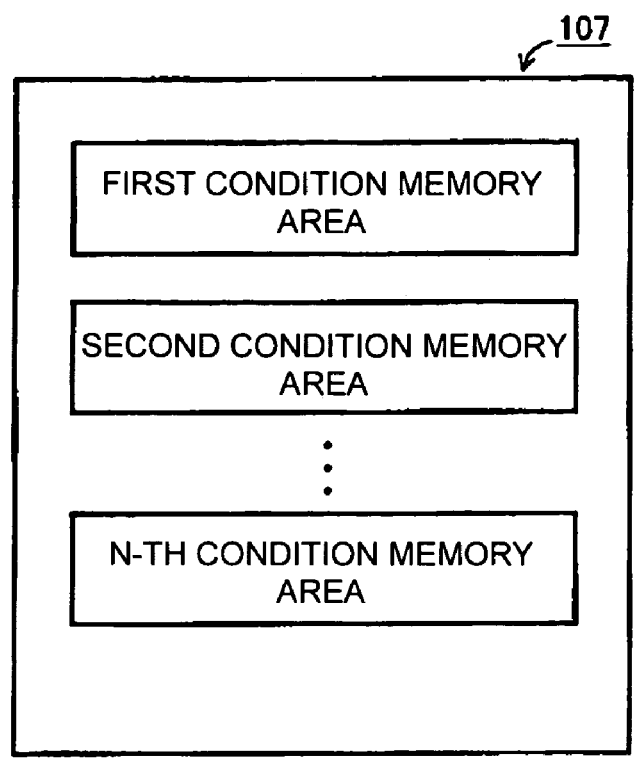
FIG. 3 is a diagram illustrating a first concrete example of areas for storing blood pressure values in a memory 107.

A concrete example of the associating manner is, as shown in FIG. 3, a method of grouping the blood pressure values input from the blood pressure calculating section 105 based on the condition information input from the condition switch 13 (first condition, second condition . . . N-th condition), and storing the group into predetermined areas in the memory 107, respectively. In the following explanation, as shown in FIG. 3, the blood pressure values are grouped based on the condition information so as to be stored into the memory areas. Needless to say, however, the associating method is not limited to this method. For example, the associating method may be a method of pairing the blood pressure values and the condition information and storing the pairs into the memory 107, or a method of storing association between the blood pressure values and the condition information as a table.

A blood pressure data intra-group average calculating section 108 reads the blood pressure values stored in the memory 107, and calculates an average of the blood pressure values per memory area as shown in FIG. 3. That is to say, intra-group averages in the blood pressure data groups including the blood pressure data measured under the same measuring condition are calculated in the respective blood pressure data groups. The blood pressure data intra-group average calculating section 108 inputs the calculated result into a risk calculating section 109.

The risk calculating section 109 reads determining information for determining risk pre-stored in the memory 107, and calculates a risk value of cardiovascular system disease based on the calculated results input from the blood pressure data intra-group average calculating section 108. The risk calculating section 109 inputs the calculated result into the display section 14, so that the display section 14 displays the risk value as well as the measured result of the blood pressure values.

Further, a clock 16 inputs time information representing time at which the measurement is made into the memory 107. In this case, the memory 107 associates the blood pressure values input from the blood pressure calculating section 105 with the time information input from the clock 106, and stores the association into predetermined areas based on the time information.

A risk analyzing process in the blood pressure monitor 1 is explained below as first and second embodiments.

First Embodiment

Figure 4:
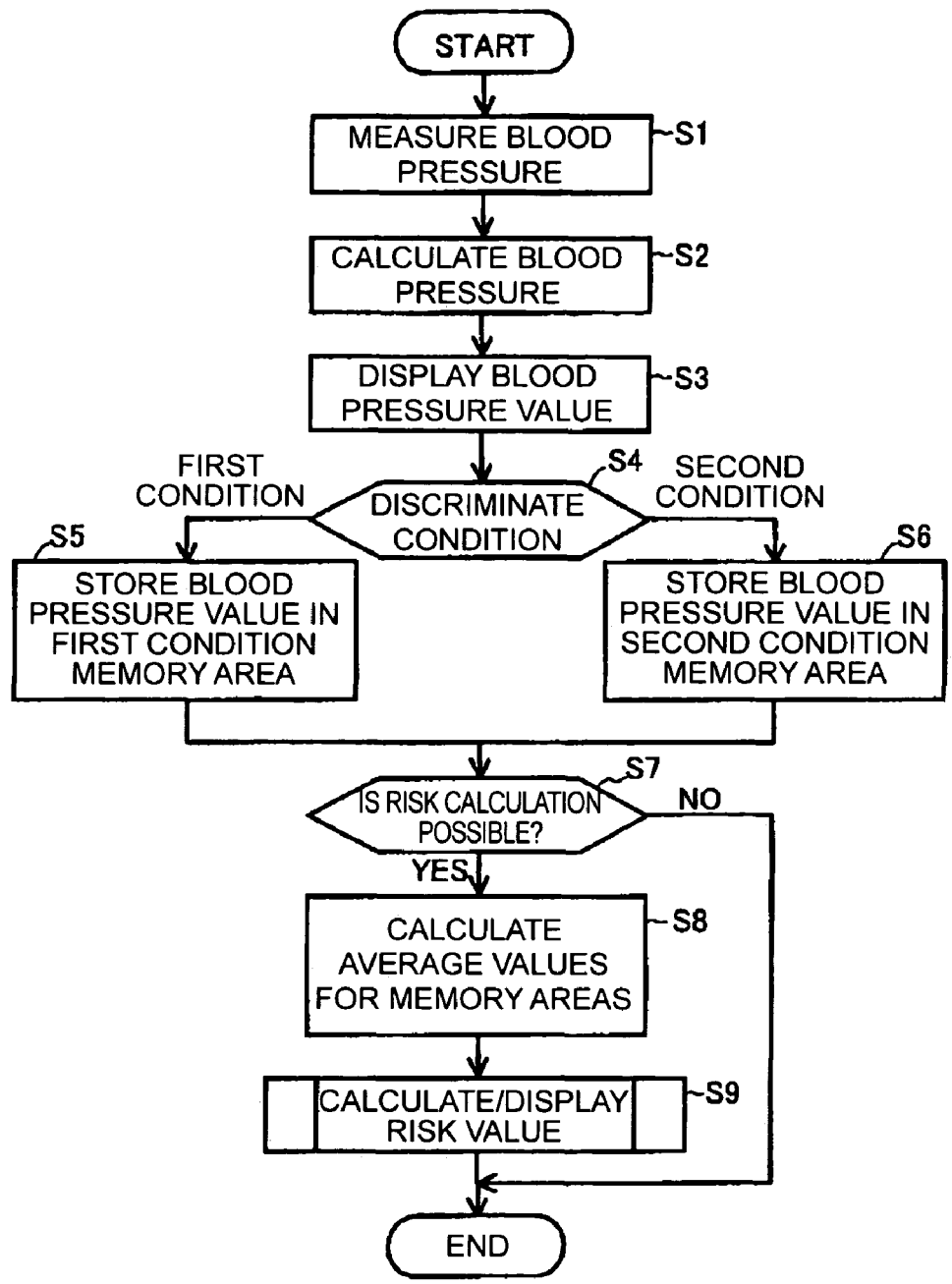
FIG. 4 is a flowchart illustrating a risk analyzing process in the blood pressure monitor 1 according to a first embodiment.

The first embodiment of the risk analyzing process in the blood pressure monitor 1 is shown in a flowchart of FIG. 4. The process shown in the flowchart of FIG. 4 is executed in such a manner that the microprocessor 15 reads a program stored in a storage device (not shown) and makes the respective sections shown in FIG. 2 operate.

With reference to FIG. 4, the user operates the starting switch 12 so as to measure blood pressure at S1. When the measurement of blood pressure starts at S1, the exhaust/pressurizing section control section 101 in the microprocessor 15 controls the pressurizing section 103 so as to pressurize the cuff 2. In such a manner, a series of the measuring operation is started. The measuring operation at S1 is general, and since its outline is as mentioned above, the explanation thereof is not repeated.

When the measurement of blood pressure at S1 is completed, the blood pressure calculating section 105 in the microprocessor 15 calculates patient's blood pressure values based on the detected result in the cuff pressure detecting section 104 at S2. At S2, the blood pressure calculating section 105 calculates systolic blood pressure, diastolic pressure and the like. The blood pressure value may be calculated from one detected result here. It is preferable, however, that the blood pressure is measured at plurality of times at S1 in order to suppress dispersion of the measurement and an average of the blood pressure values obtained from the detected results is calculated so as to be used as the blood pressure value.

The calculating method at S2 is a method of removing the cuff pressure from the pressure detected in the cuff pressure detecting section 104 and calculating patient's arterial blood pressure to be superposed on the cuff pressure signal. This blood pressure value calculating method is used in general blood pressure monitors, and thus this does not limit the present invention.

When the calculation of the blood pressure value is completed at S2, a process at the time of the completion of the measurement such as removal of the cuff pressure is executed at S3, and the measured value is displayed on the display section 14. Further, the blood pressure calculating section 105 inputs the calculated blood pressure value into the memory 107.

The microprocessor 15 discriminates a condition which is specified for the measurement by an operation by the user at S4. In the explanation, a condition 1 or a condition 2 is supposed to be specified, but a number of conditions to be specified is not limited to two, and even if its number is two or more, the same process, mentioned later, is executed.

The memory 107 stores the blood pressure value input from the blood pressure calculating section 105 into a first condition memory area or a second condition memory area at S5 or S6 according to the specified content determined at S4 ("the first condition" or "the second condition" at S4).

A determination is made at S7 whether the microprocessor 15 can calculate risk. Since the risk calculating process, mentioned below, is a process using an operated value of the memory areas in the memory 107, one or more blood pressure values should be stored in the memory area to be used in the risk calculating process. For this reason, the microprocessor 15 checks whether the one or more blood pressure values are stored in the memory areas to be used in the risk calculating process at S7.

As a result of the determination at S7, when no blood pressure value is stored in the first condition memory area or the second condition memory area to be used in the risk calculating process (NO at S7), the process is ended here.

On the other hand, as a result of the determination at S7, when one or more blood pressure values are stored in the first condition memory area and the second condition memory area to be used in the risk calculating process (YES at S7), the blood pressure data intra-group average calculating section 108 calculates an average value of the stored blood pressure values in each of the first condition memory area and the second condition memory area at S8. Further, the blood pressure data intra-group average calculating section 108 inputs the calculated results into the risk calculating section 109. In the present embodiment, the average values of the blood pressure values stored in the respective memory areas are calculated and are used in the process thereafter. The calculation, however, is not limited to the average values, and another values representing the interrelation of the blood pressure values stored in the memory areas may be calculated so as to be used in the process thereafter. Concretely, a weighting average value using a predetermined coefficient, a difference between a maximum value and a minimum value and the like may be used.

The risk calculating section 109 calculates a risk value by using the average values of the blood pressure values in the first condition memory area and the second condition memory area calculated in the blood pressure data intra-group average calculating section 108 as primary parameters which are input parameters at S9. The risk value calculating method at S9 includes various methods, and it is not limited in the present invention. Its concrete examples are explained later. When a number of conditions specified for the blood pressure measurement is two or more, a number of the input parameters to be used for the calculation of the risk value at S9 is not limited to two and thus may be two or more. In another manner, a suitable input parameter is selected from a plurality of input parameters so as to be used for the calculation of the risk value at S9.

The risk analyzing process of the first embodiment is ended. The risk analyzing process at S7 to S9 may be automatically executed every time when the blood pressure measurement at S1 to S6 is made. In another method, a risk calculating switch, not shown, which is provided to the blood pressure monitor 1, is operated by the user, and the operation of the risk calculating switch is detected at S7, so that the risk analyzing process is executed.

The blood pressure monitor 1 of the present invention executes the risk analyzing process of the first embodiment and averages the measured blood pressure values according to different conditions so as to be capable of simply analyzing risk using the average values as the primary parameters which is the input parameters of the risk calculation.

The risk analysis of the first embodiment is effective for the case or the like where a hand of a person to be measured is cooled by chilled water or the like and a difference in the blood pressure as reaction to the cooling is observed in order to detect abnormality of blood pressure modulating function due to sympathetic nerve. That is to say, the first condition and the second condition are the cases before and after the hand is cooled by chilled water, and average values in the respective cases are used as the input parameters of the risk calculation so that the blood pressure is measured and the risk can be analyzed effectively. Further, when a patient takes remedy for decrease in blood pressure, the risk analysis, in which the first and second conditions are the cases before and after taking remedy, is effective in the case where a dose and a type of remedy are changed on certain day and after, and a state of blood pressure is observed or in the case where a state of blood pressure before and after motion is observed. In such cases, since the blood pressure which is measured under the conditions (for example, before and after the cooling, a dose and a type of remedy) in disputably disperses due to various reasons, it is preferable that a plurality of blood pressure values are obtained under respective conditions, and the average values are calculated to be compared with each other. This is because reliability is improved.

Second Embodiment

Figure 5:
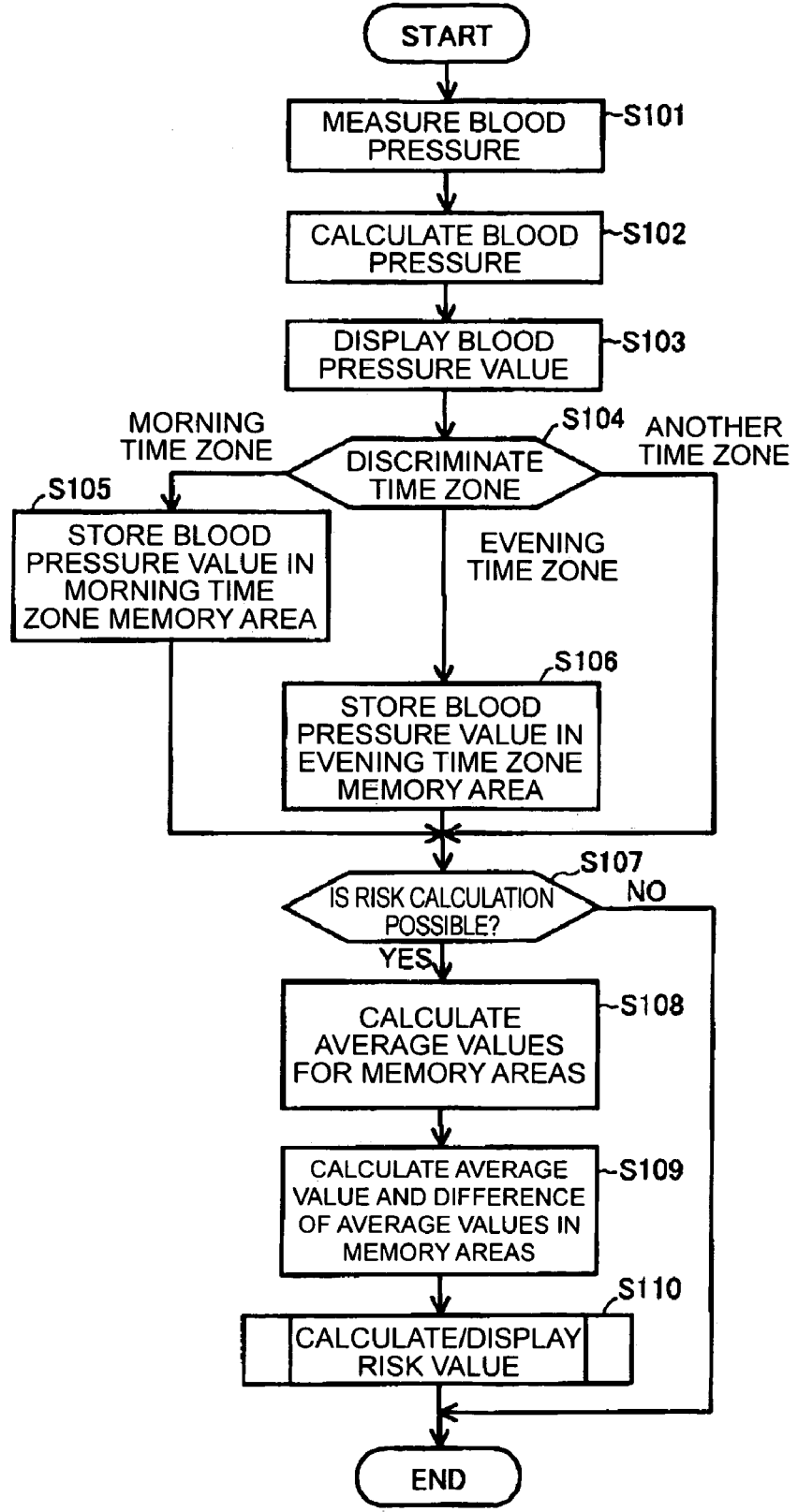
FIG. 5 is a flowchart illustrating the risk analyzing process in the blood pressure monitor 1 according to a second embodiment.

A second embodiment of the risk analyzing process in the blood pressure monitor 1 is shown in a flowchart of FIG. 5. The process shown in the flowchart of FIG. 5 is executed also in such a manner that the microprocessor 15 reads programs stored in the storage device (not shown) and operates the respective sections shown in FIG. 2.

With reference to FIG. 5, the user operates the starting switch 12 so that the blood pressure is measured at S101. When the measurement of the blood pressure is started at S101, the exhaust/pressurizing section control section 101 in the microprocessor 15 controls the pressurizing section 103 to pressurize the cuff 2, and a series of the measuring operation is started. The measuring operation at S101 is general similarly to the measuring operation at S1 in the first embodiment, and thus the explanation thereof is not repeated.

When the measurement of blood pressure is completed at S101, the blood pressure calculating section 105 in the microprocessor 15 calculates a patient's blood pressure value based on the detected result in the cuff detecting section 104 at S102. The blood pressure value may be calculated from one-time detected result. It is preferable, however, that the blood pressure is measured at a plurality of times at S1 in order to suppress dispersion of measurement, and an average of the blood pressure values obtained from the respective detected results is calculated so as to be used as the blood pressure value.

The calculating method at S102 includes the method of removing cuff pressure from the pressure detected in the cuff pressure detecting section 104 so as to calculate patient's arterial pressure superposed on the cuff pressure signal similarly to the calculating method at S2 in the first embodiment. Such a calculating method for the blood pressure value is carried out in general blood pressure monitors, and this does not limit the present invention.

When the calculation of the blood pressure value is completed at S102, the process for removing the cuff pressure or the like is executed at the time of completion of the measurement at S103, and the measured value is displayed on the display section 14. The blood pressure calculating section 105 inputs the calculated blood pressure value into the memory 107.

The microprocessor 15 discriminates a time zone where the blood pressure value is measured based on the time information associated with the blood pressure values input from the clock 106 at S104. Since it is estimated that the time at which the user makes the measurement disperses, it is preferable that a boundary value of the time zone pre-stored in the memory 107 is referred to and the time zone where the measurement is made is discriminated. Concretely, the morning time zone is set as 6 a.m. to 8 a.m., the evening time zone is set as 10 p.m. to 12 a.m., and the other time zone is set as the other time. This is preferable because the time zones which are suitable for surmising the cardiovascular risk just after user's uprising and before user's bedtime can be automatically recognized. That is to say, it is preferable that the morning time zone is set as about two hours before uprising to about two hours after uprising, and the evening time zone is set as about two hours before bedtime to about two hours after bedtime. The explanation refers to the blood pressure values in the morning time zone and the evening time zone are used for calculating the risk value, but the time zone for the blood pressure to be used is not limited to these time zones. The similar process to the process explained below is executed even in the case where the blood pressure value in another time zone is used.

Figure 6:
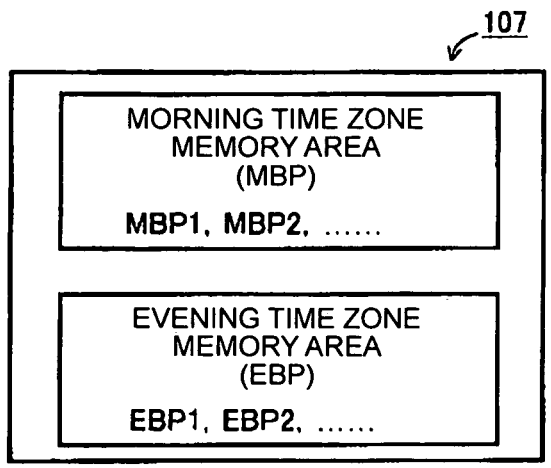
FIG. 6 is a diagram illustrating a second concrete example of areas for storing the blood pressure values in the memory 107.

At S105 or S106, the memory 107 groups the blood pressure values input from the blood pressure calculating section 105 so as to store them into predetermined memory areas according to the time zone determined at S104 (at S104 "the morning time zone" or "the evening time zone"). The areas in the memory 107 where the blood pressure values are stored in this case are constituted as shown in FIG. 6, and the blood pressure values. MBP1, MBP2, . . . measured in the morning time zone are stored in the morning time zone memory area, and the blood pressure values EBP1, EBP2, . . . measured in the evening time zone are stored in the evening time zone memory area.

On the other hand, a blood pressure value in a time zone unbelonging to the time zones determined at S104, namely, the blood pressure value which is not used for the risk value calculating process hereinafter may be removed from the blood pressure values to be stored in the memory 107. In another manner, such a blood pressure value may be stored as a blood pressure value not to be used for calculating the risk into another memory area which is provided.

A determination is made at S107 whether the microprocessor 15 can calculate the risk. That is to say, similarly to the process at S7 in the first embodiment, the microprocessor 15 checks whether one or more blood pressure values are stored in the respective memory areas to be used in the risk calculating process.

As a result of the determination at S107, when no blood pressure value is stored in the morning time zone memory area or the evening time zone memory area to be used in the risk calculating process (No at S107), the process is ended.

On the other hand, as a result of the determination at S107, when one or more blood pressure values are stored in the morning time zone memory area and the evening time zone memory area to be used in the risk calculating process (YES at S107), the blood pressure data intra-group average calculating section 108 calculates average values of the stored blood pressure values in the morning time zone memory area and the evening time zone memory area, and inputs the calculated results into the risk calculating section 109 at S108. The average value of the blood pressure values MBP1, MBP2, . . . stored in the morning time zone memory area to be calculated here is determined as MBP, and the average value of the blood pressure values EBP1, EBP2, . . . stored in the evening time zone memory area is determined as EBP. In this embodiment, the average values of the blood pressure values stored in the respective memory areas are calculated so as to be used for the processes thereafter. The embodiment is, however, not limited to the average values, and another values representing interrelation of the blood pressure values stored in the memory areas may be calculated so as to be used for the processes thereafter. Concretely, a weighting average value using a predetermined coefficient or a difference between a maximum value and a minimum value may be used.

Further, the risk calculating section 109 calculates an average (hereinafter, an ME average value) and a difference (hereinafter, an ME difference) between MBP and EBP at S109. The risk calculating section 109 calculates a risk value using the ME average value and the ME difference as input parameters at S110. The risk value calculating method at S110 includes various methods similarly to the risk-value calculating method at S9 in the first embodiment, and thus this is not limited in the present invention. Its concrete example is explained later. The input parameters are not limited to the ME average value and the ME difference, and may be another operated result representing the interrelation between the MBP and EBP. Further, a number of the input parameters to be used for calculating the risk value at S109 is not limited to two, and may be two or more.

The risk analyzing process in the second embodiment is ended. The risk analyzing process at S107 to S110 may be executed automatically every time when the blood pressure is measured at S101 to S106. In another manner, the user operates a risk calculating switch, not shown, which is provided to the blood pressure monitor 1, and the operation of the risk calculating switch is detected at S107 so that the process may be executed.

The blood pressure monitor 1 of the present invention executes the risk analyzing process in the second embodiment, so as to once calculate the averages of the blood pressure values under different conditions without simply using the blood pressure value obtained under different conditions as the input parameters of the risk calculation. Thereafter, the operated results are used as the input parameters for the risk calculation, and the risk can be analyzed. That is to say, a plurality of blood pressure groups, each of which is composed of at least one blood pressure values obtained under different conditions, are obtained, and the risk of the cardiovascular disease can be estimated based on interrelation of the blood pressure values included in the groups. Further, the different conditions can be automatically detected by the clock function so as to be grouped.

The risk analysis in the second embodiment is effective particularly in order to prevent cardiovascular events such as cerebral accident, cardiac failure, cerebral infarction, cerebral hemorrhage, subarachnoid hemorrhage, transient cerebral ischemic attack, falling-down, faint, vertigo, stagger, myocardial infarct, angina pectoris, asymptomatic heart ischemia, arhythmia, cribdeath, dissecting aneurysm of the aorta, and ruptured aortic aneurysm.

Figure 7:
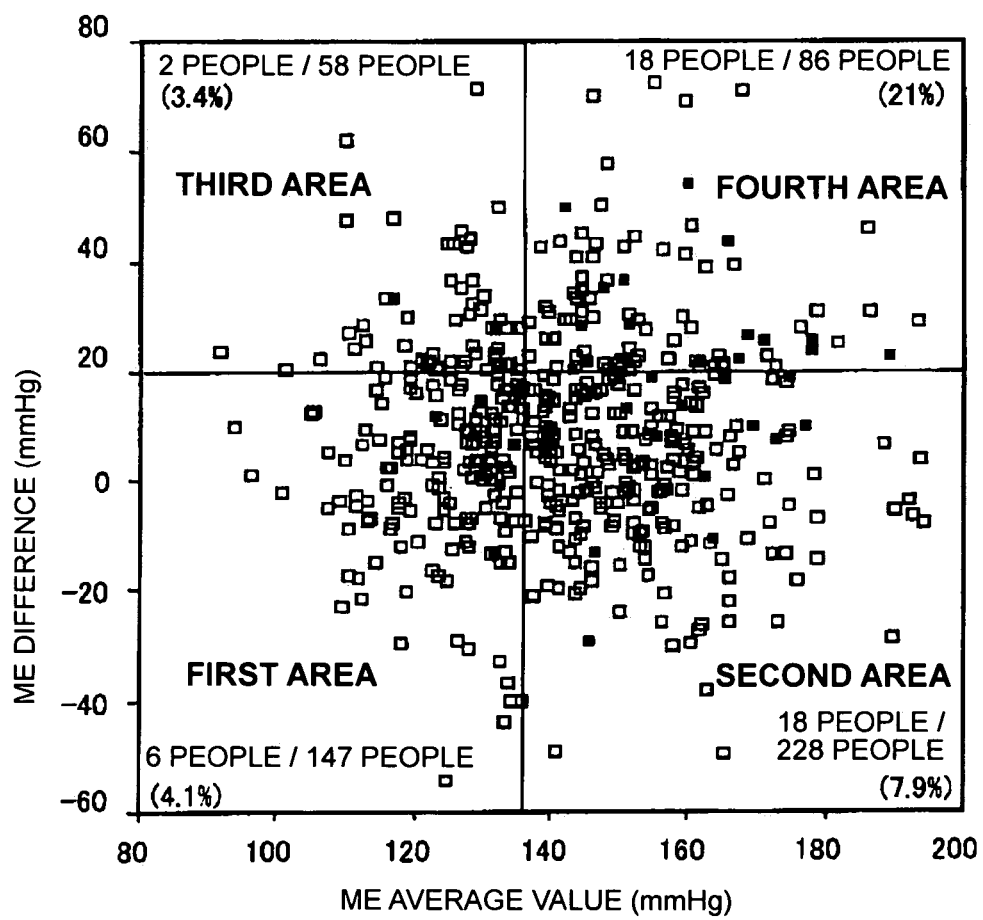
FIG. 7 is a diagram illustrating interrelation of blood pressure values measured in a time zone before bedtime and in a time zone just after uprising and a relationship between the blood pressure values and risk of cerebral apoplexy.

Concretely, according to the study result by the inventors of the present application, as shown in FIG. 7, the average values of the blood pressure values measured in the time zone before bedtime (evening time zone) and the time zone just after uprising (morning time zone) (ME average values) are plotted along a horizontal axis, and the differences therebetween (ME differences) are plotted along a vertical axis. In such a plane, a threshold value of 135 mmHg is provided on the horizontal axis, and a threshold value of 20 mmHg is provided on the vertical axis, so that the plane is divided into four areas (first through fourth areas). Blood pressure data of many hupertensives are plotted on the plane. It is found that many data of stroke patients represented by black dots in FIG. 7 are present particularly in the fourth area, namely, the area where both the ME average value and the ME difference are large. In FIG. 7, numerical values at four corners represent a number of subjects included in the diastolic pressure area, a number of subjects suffering from cerebral accident, and a percentage (%) of subjects suffering from cerebral accident. The threshold values provided on the horizontal axis and the vertical axis are not, limited to 135 mmHg and 20 mmHg. It is preferable that the threshold value on the horizontal axis is 135 mmHg to 140 mmHg, and the threshold value on the vertical axis is 10 mmHg to 20 mmHg.

For example, a percentage of the cerebral accident in the fourth area reaches 5.1 times as large as that in the first area (namely, the area where both the ME average value and the ME difference are low). In other words, this means that the risk (probability) of cardiovascular accidents such as cerebral accident and myocardial infarct can be estimated by the two parameters including the ME average value and the ME difference. Since the blood pressure disperses due to influence of various factors, the measurement of blood pressure is preferably repeated in these time zones for a plurality of days, and the average values in the time zones are obtained so that the ME average value and the ME difference are obtained. This method improves accuracy of the risk estimation.

The blood pressure monitor 1 of the present invention executes the risk analyzing process in the second embodiment so as to obtain the blood pressure data groups including at least one blood pressure value measured in the time zone before bedtime (evening time zone) and the time zone just after uprising (morning time zone) (data included in the morning time zone memory area and the evening time zone memory area). After the averages of the blood pressure values in the respective groups are calculated (intra-group average (MBP, EBP)), and primary parameters, which are the two input parameters including the average values (ME average value) and the difference (ME difference) in the groups, are calculated. For this reason, the blood pressure monitor 1 of the present invention is effective particularly in calculating a risk value of the cardiovascular diseases based on the two primary parameters including the ME average value and the ME difference so as to estimate the risk.

That is to say, since the blood pressure monitor 1 of the present invention discriminates the measuring time zones of the blood pressure values automatically so as to calculate the risk value, the user can estimate the risk simply similarly to the operation of prior blood pressure monitors having a memory function and a clock function.

Further, the blood pressure monitor 1 executes the risk analyzing process in the second embodiment and calculates the ME average value and the ME difference based on the blood pressure values measured in the morning time zone and the evening time zone. When a determination is made that both of the ME average value and the ME difference are high, the risk of cardiovascular accidents such as cerebral accident is high. For this reason, it is preferable that the blood pressure monitor 1 warns the user in order to prevent the cardiovascular accidents. That is to say, when the user does not take medical treatment, the blood pressure monitor 1 warns the user of immediate medical treatment. Further, when the user has already taken medical treatment, the blood pressure monitor 1 notifies the user that the user should take counsel with a doctor about a change in medication contents according to a degree of the highness of the risk.

Further, since blood pressure changes due to various factors and its measured values disperse, when the above risk is determined based only on the blood pressure values obtained once in the morning and the evening, the accuracy is slightly insufficient. Even in such a case, the blood pressure monitor 1 of the present invention stores the blood pressure values, which are measured in the morning time zone and the evening time zone for a plurality of days, into the memory 107. Further, the blood pressure monitor 1 calculates the ME average value and the ME difference of the average values (MBP, EBP) in the morning time zone and the evening time zone stored in the memory 107 so as to calculate the risk value. For this reason, the reliability of the determined result can be improved remarkably.

Concrete examples of the risk value calculating method in the risk analyzing process are explained below. These are a concrete method for the risk value calculating process which is executed by the risk calculating section 109 at S9 in the risk analyzing process in the first embodiment and at S110 in the risk analyzing process in the second embodiment.

Figure 8:
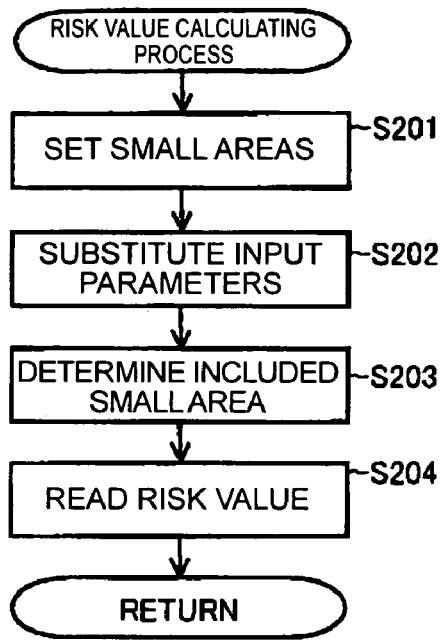
FIG. 8 is a flowchart illustrating a concrete example of a first risk value calculating method.

The concrete example of a first risk value calculating method is shown in a flowchart of FIG. 8. With reference to FIG. 8, the risk calculating section 109 sets at least one threshold value as criterion for each axis in a two-dimensional plane which is defined by axes of the primary parameters as the two input parameters at S201. Further, small areas which are a plurality of primary parameter areas divided by the threshold values are defined as criterion areas.

The risk calculating section 109 associates actual values represented by the two input parameters with the two-dimensional plane and determines which small area where the actual values are included at S202.

Finally, at S203, the risk calculating section 109 reads risk value in the small area including the actual values represented by the two input parameters included in the risk values corresponding to the small areas stored in the memory 107 based on the determined result at S202. The read risk values are determined as risk calculated values.

The risk calculating section 109 transmits information about the two-dimensional plane and information about the actual values represented by the two input parameters to the display section 14. As a result, it is preferable that the actual values are displayed on the two-dimensional plane in the display section 14.

The risk calculating section 109 executes the risk value calculating process which adopts the first risk value calculating method, so as to define the two-dimensional plane shown in FIG. 7, in which the ME average value and the ME difference as the input parameters are plotted along the horizontal axis and the vertical axis, respectively, at S110 of the risk analyzing process in the second embodiment. The risk calculating section 109 sets the ME average value on the horizontal axis to 135 mmHg, and the ME difference on the vertical axis to 20 mmHg as the threshold values, and defines the first through fourth areas divided by the threshold values.

Various risk values of cardiovascular diseases corresponding to the small areas can be considered, but according to the data shown in FIG. 7, for example, an incidence of cerebral accident in the first area on the lower left, where both the ME average value and the ME difference are low, is 4.1%. For this reason, a ratio of relative incidence to the incidence can be determined as the risk in the respective small areas. Concretely, when the risk value in the first area as standard is 1.0, the risk value in the second area is 1.9 (=7.9%/4.1%), the risk value in the third area is 0.8 (=3.4%/4.1%), and the risk value in the fourth area is 5.1 (=21.%/4.1%). These risk values are, therefore, pre-stored in the memory 107, and the corresponding small area is specified based on the actual values including the ME average value and the ME difference so that a corresponding risk value may be displayed at S202.

The concrete example of the first risk value calculating method is a method for calculating the risk value using the two input parameters, but the same method can be used for the case where the risk value is calculated by using two or more input parameters. That is to say, when the risk value is calculated by using N-numbered input parameters, at least one threshold value as criterion is set on each axis in an N-dimensional area defined by the axes of the N-numbered input parameters at S201. A plurality of small areas, which are N-dimensional primary parameter areas divided by the threshold values, are defined as criterion areas. The actual values represented by the N-numbered input parameters are associated with the N-dimensional area, the risk value corresponding to the small area included in the actual values is read from the memory 107 so as to be determined as the risk calculated value at S202.

In the first risk-value calculating method, when a number of threshold values to be set is reduced, namely, an area of small areas is increased so that a number of small areas is reduced, the process in the blood pressure monitor 1 can be simplified. In this calculating method, however, since the risk values in the small areas are supposed to be constant, when a number of threshold values to be set is reduced, the risk value which changes locally in the small areas actually is hardly reflected. As a result, the accuracy of the risk value to be calculated is in danger of being low.

As a second risk value calculating method, therefore, a method of calculating the risk defined by continuous quantity based on the values represented by the input parameters is explained below. This is a method corresponding to the case where a number of threshold values to be set is infinite in the first risk value calculating method. In other words, this is a method of calculating the risk value R according to N-variate function F as expressed in the following equation where the input parameters are variables.

$$R=F(\text{input parameter 1, input parameter 2}, \ldots, \text{input parameter } N)$$

Figure 9:
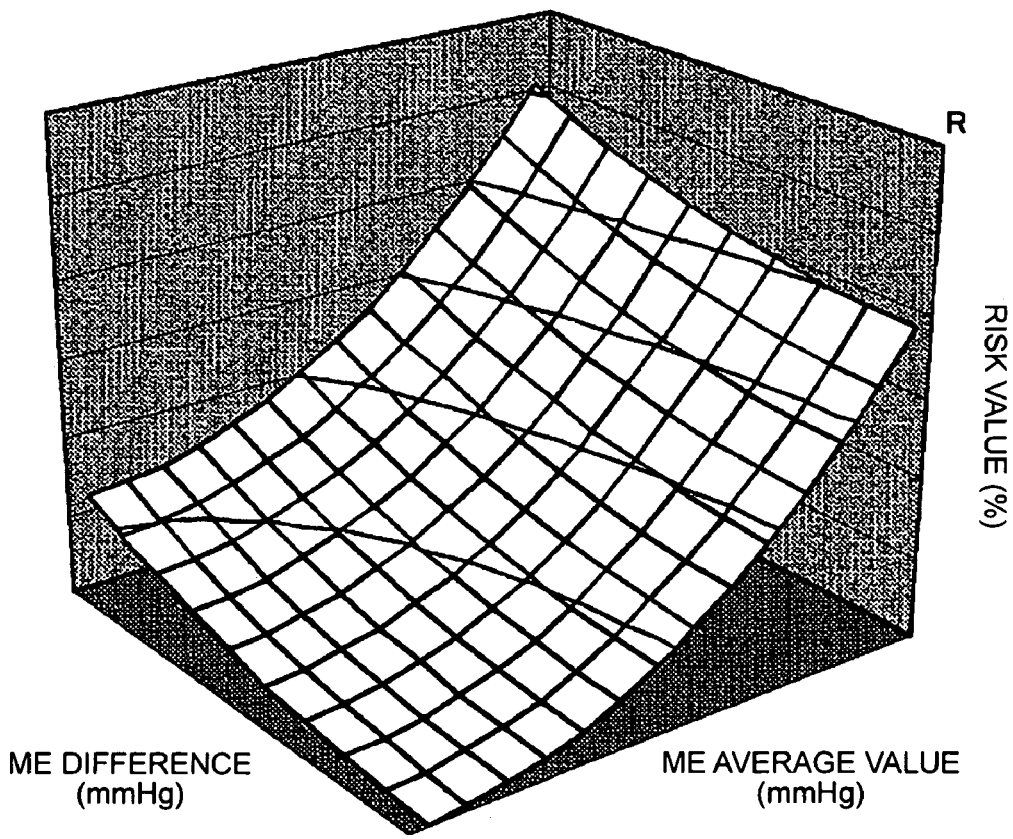
FIG. 9 is a diagram illustrating a concrete example of bivariate function F in which an ME average value and an ME difference are used as variables.

The N-variate function F can be obtained in such a manner that actually the risk values for N-numbered parameters are calculated locally and the calculated risk values are approximated. For example, in the case of the above-mentioned concrete example, the risk values which are incidence of cerebral accident are calculated locally and are approximated for the blood pressure data represented by the two input parameters including the average value (ME average value) and the difference (ME difference) of the blood pressure measured in the morning and the evening. As a result, bivariate function F in which the ME average value and the ME difference are variable can be obtained as shown in the concrete example of FIG. 9.

When the N-variate function obtained in such a manner is pre-stored as the determined information into the memory 107, the risk calculating section 109 can obtain the risk value by inputting the actual values represented by the N-numbered input parameters into the N-variate function read from the memory 107. Further, the risk calculating section 109 transmits the N-variate function read from the memory 107 and the actual values represented by the N-numbered input parameters to the display section 14. As a result, it is preferable that the actual values are displayed in the area represented by the N-variate function in the display section 14.

It is preferable that the risk is analyzed in the blood pressure monitor 1 in order to observe a curative effect and check whether condition of diseases do not get worse. In this case, the risk of the cardiovascular disease should be compared and tracked for a certain time period. For this reason, it is preferable that the blood pressure monitor 1 has a function for displaying the primary parameters calculated for a plurality of periods on one coordinate, and checking transition. As presupposition for the risk analysis, the clock 106 in the blood pressure monitor 1 inputs date and time information representing date and time at which the measurement is made in the blood pressure monitor 1 into the memory 107. The blood pressure values input from the blood pressure calculating section 105 are associated with the date and time information input from the clock 106 so that they are stored into a predetermined area of the memory 107. Further, the blood pressure values input from the blood pressure calculating section 105 are associated with the date and time information input from the clock 106 and the condition information input from the condition switch 13 so that they may be stored in predetermined areas of the memory 107.

Figure 10:
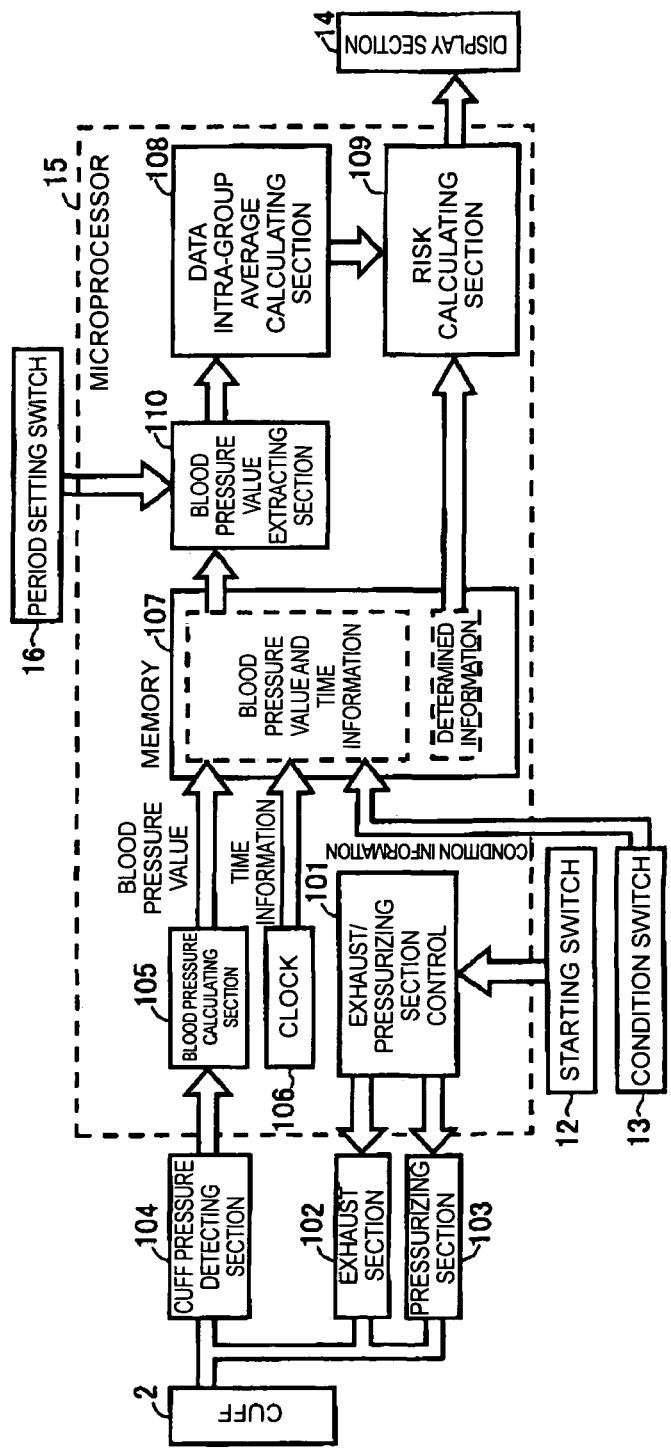
FIG. 10 is a block diagram illustrating a concrete example of a constitution when the blood pressure monitor 1 has a function for checking a transition of primary parameters.

The concrete example of the constitution when the blood pressure monitor 1 of the present invention has the above-mentioned function is shown in a block diagram of FIG. 10. The constitution shown in FIG. 10 further includes a blood pressure value extracting section 110 for realizing the above function. A difference from the constitution shown in FIG. 2 is, therefore, explained with reference to FIG. 10.

The blood pressure value extracting section 110 shown in FIG. 10 receives information for a plurality of set periods from the period setting switch 16. The blood pressure value extracting section 110 extracts blood pressure values corresponding to the received periods from the blood pressure values stored in the memory 107. The blood pressure value extracting section 110 inputs the extracted blood pressure values corresponding to the periods into the dada intra-group average calculating section 108.

The data intra-group average calculating section 108 executes a process for calculating averages of the blood pressure values in the memory areas shown in FIG. 3 for the respective periods of the blood pressure values input from the blood pressure value extracting section 110. The blood pressure data intra-group average calculating section 108 inputs the calculated results into the risk calculating section 109.

The risk calculating section 109 calculates the risk values similar to the above-mentioned ones based on the calculated results input from the blood pressure data intra-group average calculating section 108.

Figure 11:
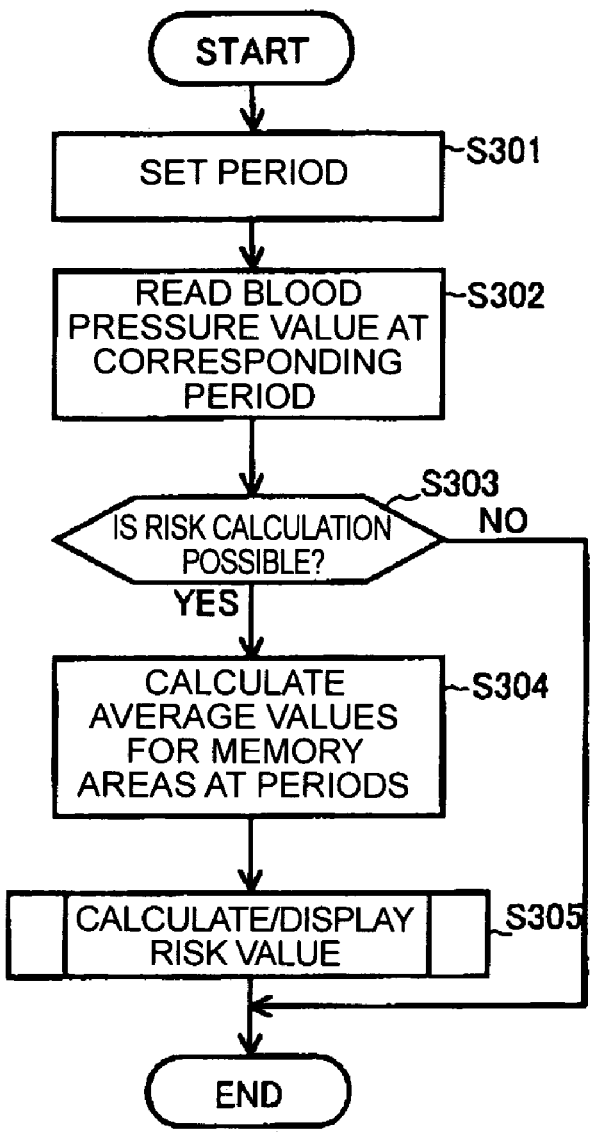
FIG. 11 is a flowchart illustrating a process when the blood pressure monitor 1 displays the transition of the primary parameters.

FIG. 11 is a flowchart illustrating the process when the blood pressure 1 displays the transition of the primary parameter. The process shown in the flowchart of FIG. 11 is also executed in such a manner that the microprocessor 15 reads the program stored in the storage device (not shown) and operates the respective sections shown in FIG. 10.

With reference to FIG. 11, when the user operates the period setting switch 16, the blood pressure monitor 1 sets a plurality of periods at which the transition of the primary parameter is displayed at S301.

The blood pressure value extracting section 110 extracts the blood pressure values corresponding to the received periods from the blood pressure values stored in the memory 107 at S302. The blood pressure value extracting section 110 refers to the date and time information associated with the blood pressure values stored in the memory 107 and extracts the blood pressure values associated with the date and time information corresponding to the periods received from the period setting switch 16 at S302.

The microprocessor 15 determines whether the risk can be calculated for the corresponding periods at S303. Since the risk calculating process uses the operated values in the memory areas in the memory 107, one or more blood pressure values should be stored in the memory area to be used for the risk calculating process. For this reason, the microprocessor 15 checks whether one or more blood pressure values are stored in each memory area to be used for the risk calculating process per period at S303.

As a result of the determination at S303, when no blood pressure value is stored in any one of the memory area to be used for the risk calculating process per period (No at S303), the process is ended.

On the other hand, as a result of the determination at S303, when one or more blood pressure values are stored in each memory area to be used for the risk calculating process per period (YES at S303), at S304 the blood pressure data intra-group average calculating section 108 calculates the average values of the blood pressure values stored in the memory areas per period. Thereafter, it inputs the calculated results into the risk calculating section 109.

The risk calculating section 109 inputs the average values of the blood pressure values stored in the memory areas per period calculated in the blood pressure data intra-group average calculating section 108 into the display section 14 at S305. The average values are input as the primary parameters in order to display the transition of the primary parameter per set period.

Further, when the transition of the risk values based on the time zones where the blood pressure is measured is displayed as mentioned above, similarly to the process at S109, the risk calculating section 109 calculates the average values in the memory areas calculated at S304, namely, the average (ME average value) and the difference (ME difference) between the average value MBP in the morning time zone memory area and the average value EBP in the evening time zone memory area at S305. Thereafter, the risk calculating section 109 inputs the calculated results as the primary parameters into the display section 14.

Figure 12:
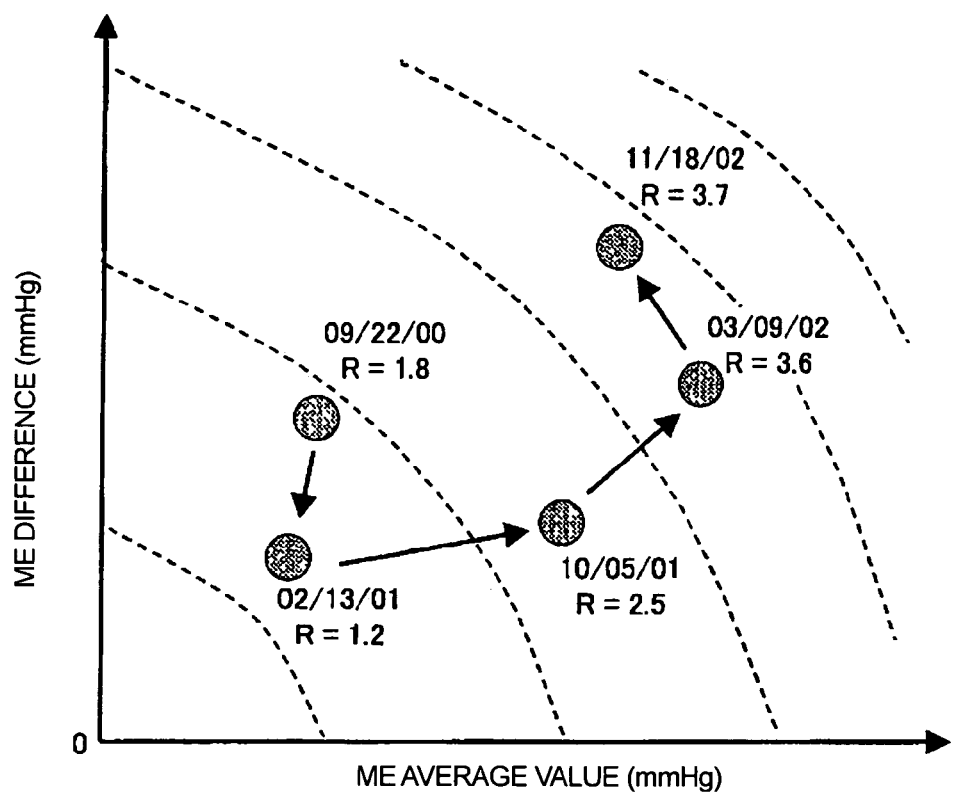
FIG. 12 is a diagram illustrating a concrete example of display of the transition of the primary parameters.

When the above process is executed by the blood pressure monitor 1 of the present invention, as shown in the concrete example of FIG. 12, the transition of the primary parameters for each of the set periods can be displayed on the display section 14. For this reason, when a plurality of primary parameter groups under different conditions are present, this process is effective when the primary parameter groups are compared with each other or their change is observed.

In the concrete example of the display of the transition of the primary parameters shown in FIG. 12, the transition between the ME average value and the ME difference as the primary parameters is displayed. Further, as shown in FIG. 12, in order to display the transition of the primary parameters more clearly, it is preferable that data points are connected by arrows according to their order and a measuring data is displayed. Further, it is preferable that the risk values are calculated by the method similar to the above one using the primary parameters, and the risk values are displayed at the respective data points.

In the above process, the blood pressure monitor 1 calculates the primary parameters for the respective periods after reception of the setting of the periods for displaying the transition of the primary parameters. The blood pressure monitor 1, however, previously receives the setting of the periods every one month, for example, and may store the primary parameters calculated for the respective periods into the predetermined areas of the memory 107. It is preferable that the user performs a calling operation so as to call the primary parameters from the memory 107 and display them on the display section 14 simultaneously.

The setting of the periods for displaying the transition of the primary parameters is not limited to one month, and may be a plurality of predetermined dates such as Sep. 22, 2000, Feb. 12, 2001, and Oct. 5, 2001. In this case, the blood pressure monitor 1 extracts only the blood pressure value associated with the date and time information representing that day, namely, the blood pressure value measured on that day from the memory 107. Further, the blood pressure monitor 1 may calculate the primary parameters so as to display them. In another manner, the period for calculating the primary parameters is preset to 1 month or the other, and when a plurality of predetermined dates are set, the blood pressure monitor 1 extracts the blood pressure values for one month before the dates from the memory 107, and calculates the primary parameters so as to display them.

MODIFIED EXAMPLE

Further, the risk value calculating method executed by the blood pressure monitor 1 and the method of displaying the transition of the primary parameters can be provided as programs. These programs are recorded in a recording medium which can be read by a computer such as a flexible disc, a CD-ROM (Compact Disc-Read Only Memory), a ROM (Read Only Memory), a RAM (Random Access Memory) and a memory card attached to the computer, so as to be capable of being provided as program products. In another manner, the programs are recorded in a recording medium such as a hard disc included in the computer so as to be capable of being provided. Further, the programs can be provided by downloading via a network.

The program products to be provided are installed into a program storage section such as a hard disc so as to be executed. The program products include the programs and the recording medium into which the programs are recorded.

Figure 13:
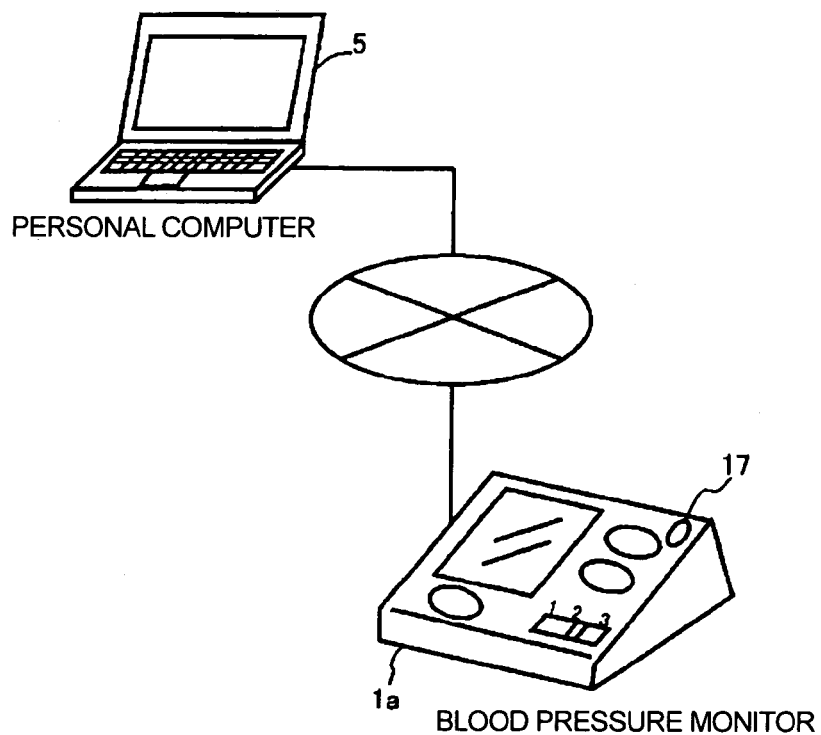
FIG. 13 is a diagram illustrating a concrete example of a constitution of a cardiovascular disease risk analyzing system according to a modified example.

FIG. 13 is a diagram illustrating a concrete example of the constitution of the cardiovascular disease risk analyzing system in the modified example. With reference to FIG. 13, the cardiovascular disease risk analyzing system in the modified example is composed of a computer (hereinafter, a personal computer) 5 for storing the programs therein and a blood pressure monitor 1a. They communicate with each other via a privately used line such as LAN (Local Area Network), or a public line such as a telephone line, or a radio.

Since the personal computer 5 is a general personal computer or the like, its hardware structure is not detailed here. Such a personal computer 5 may be installed at general home or a server which is installed in medical facility such as hospital.

Further, since the process executed by the personal computer 5 is similar to the process executed in the blood pressure monitor 1, the detailed explanation thereof is not repeated. That is to say, the personal computer 5 executes the above programs, and can display the risk values on a screen using data received from the blood pressure monitor 1 and data stored in the past or can display a graph showing the transition of the primary parameters as shown in FIG. 12.

In this case, the blood pressure monitor 1a further includes a transmission button 17 shown in FIG. 13, and a communication unit such as a modem or an interface for connecting with a general public line as well as the general components of the blood pressure monitor. When the transmission button 17 is pressed down after the blood pressure is measured, the blood pressure monitor 1a transmits the measured blood pressure values into the personal computer 5.

In another manner, the blood pressure monitor 1a may further include the transmission button 17 and the communication unit as well as the components of the blood pressure monitor 1 shown in FIG. 2. In this case, the blood pressure monitor 1a stores the ME average value and the ME difference, and an evaluating quantity based the interrelation of the measured values under the respective measuring conditions, such as an evaluating quantity based on the interrelation of the blood pressure values before and after cooling, as well as the date information into the memory. The blood pressure monitor 1a may transmit these data into the personal computer 5. As a result, a quantity of data to be transmitted can be reduced, and communication time can be shortened.

The embodiments disclosed this time are considered in all respects as illustrative and not restrictive. The scope of the present invention is indicated by the appended claims rather than by the foregoing description and all changes which come within the meaning and range of equivalency of the claims are therefore intended to be embraced therein.

What is claimed is:

1. A blood pressure monitor comprising:
a blood pressure data storage unit for storing blood pressure data groups each of which includes at least one blood pressure datum measured under one measuring condition;
an evaluating quantity calculating unit for calculating an evaluating quantity based on an interrelation between the blood pressure data in a first blood pressure data group and the blood pressure data in a second blood pressure data group with different measuring condition than the first blood pressure data group; and
an intra-group average calculating unit for calculating intra-group averages of blood pressure data in the blood pressure data groups for the blood pressure data groups with the different measuring conditions.

2. The blood pressure monitor according to claim 1, wherein the evaluating quantity calculating unit calculates the evaluating quantity based on an average value and a different value of the intra-group averages in the blood pressure data groups.

3. The blood pressure monitor according to claim 2, further comprising:
a cardiovascular disease risk calculating function unit for estimating a degree of cardiovascular disease risk in a numerical manner by using both the average values and the different values of the intra-group averages in the blood pressure data groups as input variables,
wherein a cardiovascular disease risk calculating function unit calculates or displays the cardiovascular disease risk when actual values of the average values and the different values of the intra-group averages are obtained.

4. The blood pressure monitor according to claims 1, wherein the evaluating quantity is related with a degree of a risk of cardiovascular diseases.

5. The blood pressure monitor according to any one of claims 1 to 4, wherein the measuring conditions are a plurality of specified time zones.

6. The blood pressure monitor according to claim 5, wherein the plural specified time zones include a first time zone which starts from about two hours before bedtime and ends until two hours after bedtime, and a second time zone which starts from about two hours before awakening and ends until about two hours after awakening.

7. The blood pressure monitor according to claim 5, further comprising:
a clock unit for outputting time information,
wherein the blood pressure data storage unit discriminates the measuring conditions for each blood pressure data based on the time information output from the clock unit and stores the blood pressure data according to measuring conditions.

8. The blood pressure monitor according to claim 1, further comprising:
an input unit through which a user inputs the measuring conditions,
wherein the blood pressure data storage unit stores the blood pressure data based on the measuring conditions input from the input unit.

9. The blood pressure monitor according to any one of claims 1 to 2, further comprising a diagnostic unit for providing at least one or more threshold values on at least one of a plurality of primary parameter axes obtained as intra-group averages of a plurality of blood pressure data groups with the different measuring conditions or average values and different values of the intra-group averages, defining a plurality of primary parameter areas, which are prescribed by the threshold values, in a primary parameter multi-dimensional area composed of the primary parameter axes, and determining or displaying which area of the primary parameter areas where actual values of primary parameters obtained based on the measured blood pressure data are present, so as to make a diagnosis based on the blood pressure data.

10. The blood pressure monitor according to claim 9, further comprising:
a primary parameter area display unit for displaying the primary parameter multi-dimensional area,
wherein the primary parameter area display unit displays the actual values of the primary parameters on the primary parameter multi-dimensional area.

11. The blood pressure monitor according to claim 10, further comprising:
a primary parameter set storage unit for storing a plurality of primary parameter sets which are composed of the intra-group averages of the blood pressure data groups with the different measuring conditions or pairs of the average values and the different values of the intra-group averages,
wherein the primary parameter area display unit displays the primary parameter sets on the primary parameter multi-dimensional area simultaneously.

12. The blood pressure monitor according to claim 9, further comprising:
a cardiovascular disease risk defining unit in which a degree of digitized cardiovascular disease risk is associated with the primary parameter areas, respectively,
wherein the risk calculating unit determines or displays the cardiovascular disease risk based on the determination as to which area of the primary parameter areas where the actual values of the primary parameters are present.

13. The blood pressure monitor according to claim 9, wherein the threshold values provided on the primary parameter axes obtained as the average values of the intra-group averages in the blood pressure data groups are threshold values of systolic blood pressure, and they are about 135 mmHg.

14. The blood pressure monitor according to claim 9, wherein the different values of the intra-group averages in the blood pressure data groups are increments of systolic blood pressure measured at time before and after uprising with respect to systolic blood pressure measured at time before bedtime, and the threshold values provided on the primary parameter axes obtained as the different values of the intra-group averages are about 20 mm Hg.

15. A cardiovascular disease risk analyzing program encoded on a computer readable medium, the program comprising a set of instructions for performing the following:
obtaining blood pressure data;
storing blood pressure data groups including at least one blood pressure datum measured under same measuring conditions in the obtained blood pressure data into a storage section according to measuring conditions; and
calculating an evaluating quantity based on interrelation between the blood pressure data in a first blood pressure data group and the blood pressure data in a second blood pressure data group with different measuring condition than the first blood pressure data group; and
calculating intra-group averages of the blood pressure data in the blood pressure data groups for the blood pressure data groups with the different measuring conditions.

16. The cardiovascular disease risk analyzing program according to claim 15 wherein the evaluating quantity is calculated based on average values and different values of intra-group averages in the blood pressure data groups.

17. The cardiovascular disease risk analyzing program according to claim 16, for allowing the computer to further execute the cardiovascular disease risk calculating function step of estimating a degree of the cardiovascular disease risk in a numerical manner by using both the average values and the different values of the intra-group averages in the blood pressure data groups as input variables,
wherein at the cardiovascular disease risk calculating function step, when the actual values of the average values and the different values of the intra-group averages are obtained, the cardiovascular disease risk is calculated or displayed.

18. The cardiovascular disease risk analyzing program according to claim 15, further comprising receiving the measuring conditions from a user,
wherein the blood pressure data are stored based on the measuring conditions input into the storage section according to the measuring conditions.

19. The cardiovascular disease risk analyzing program according to claim 15, wherein the evaluating quantity relates to a degree of the cardiovascular disease risk.

20. The cardiovascular disease risk analyzing program according to any one of claims 15 to 19, wherein the measuring conditions are a plurality of specified time zones.

21. The cardiovascular disease risk analyzing program according to claim 20, wherein the specified time zones include a first time zone which starts from about two hours before bedtime and ends about two hours after bedtime, and a second time zone which starts from about two hours before awakening and ends until about two hours after awakening.

22. The cardiovascular disease risk analyzing program according to claim 20, further comprising outputting time information,
wherein the measuring conditions are discriminated according to the blood pressure data based on the time information, and the blood pressure data are stored into the storage section according to the measuring conditions.

23. The cardiovascular disease risk analyzing program according to any one of claims 15 to 16, further comprising providing one or more threshold values on at least one of a plurality of primary parameter axes obtained as the intra-group averages in the blood pressure data groups with the different measuring conditions or the average values and the different values of the intra-group averages, defining a plurality of primary parameter areas which are prescribed by the threshold values in a primary parameter multi-dimensional area composed of the primary parameter axes, and determining or displaying as to which area of the primary parameter areas where actual values of primary parameters obtained based on the measured blood pressure data are present so as to make a diagnosis based on the blood pressure data.

24. The cardiovascular disease risk analyzing program according to claim 23, wherein the different values of the intra-group averages in the blood pressure data groups are increments of systolic blood pressure measured at time before and after uprising with respect to systolic blood pressure measured at time before bedtime, and the threshold values provided on the primary parameter axes obtained as the different values of the intra-group averages are about 20 mmHg.

25. The cardiovascular disease risk analyzing program according to claim 23, further comprising displaying the primary parameter multi-dimensional area,
wherein at the primary parameter area display step, the actual values of the primary parameters are displayed on the primary parameter multi-dimensional area.

26. The cardiovascular disease risk analyzing program according to claim 25, further comprising storing a plurality of primary parameter sets composed of the intra-group averages in the blood pressure data groups with the different measuring conditions or pairs of the average values and the different values of the intra-group averages,
wherein at the primary parameter area display step, the primary parameter sets are displayed on the primary parameter multi-dimensional area simultaneously.

27. The cardiovascular disease risk analyzing program according to claim 23, further comprising associating a degree of the digitized cardiovascular disease risk with the primary parameter areas, respectively,
wherein at the risk calculating step, the cardiovascular disease risk is determined or displayed based on the determination as to which area of the primary parameter areas where the actual values of the primary parameters are present.

28. The cardiovascular disease risk analyzing program according to claim 23, wherein the threshold values provided on the primary parameter axes obtained as the average values of the intra-group averages in the blood pressure data groups are threshold values of systolic blood pressure and are about 135 mmHg.

* * * * *